United States Patent
Kim

(10) Patent No.: US 11,534,376 B2
(45) Date of Patent: Dec. 27, 2022

(54) ANTIBACTERIAL DEODORANT CONTAINING TITANIUM DIOXIDE PHOTOCATALYST

(71) Applicant: DAESOO HI-TECH CO., LTD., Daejeon (KR)

(72) Inventor: Chang Kyun Kim, Sejong-si (KR)

(73) Assignee: DAESOO HI-TECH CO., LTD., Daejeon (KR)

( * ) Notice: Subject to any disclaimer, the term of this patent is extended or adjusted under 35 U.S.C. 154(b) by 0 days.

(21) Appl. No.: 17/406,650

(22) Filed: Aug. 19, 2021

(65) Prior Publication Data

US 2022/0257481 A1  Aug. 18, 2022

(30) Foreign Application Priority Data

Feb. 18, 2021 (KR) .................. 10-2021-0021962

(51) Int. Cl.
| | |
|---|---|
| *A61Q 15/00* | (2006.01) |
| *A61K 8/29* | (2006.01) |
| *A61K 8/19* | (2006.01) |
| *A61K 8/34* | (2006.01) |
| *A61K 8/31* | (2006.01) |
| *A61K 8/41* | (2006.01) |

(52) U.S. Cl.
CPC .................. *A61K 8/29* (2013.01); *A61K 8/19* (2013.01); *A61K 8/31* (2013.01); *A61K 8/34* (2013.01); *A61K 8/41* (2013.01); *A61Q 15/00* (2013.01)

(58) Field of Classification Search
CPC ........ A61Q 15/00; A61Q 17/005; A61K 8/34; A61K 8/19; A61K 8/31; A61K 8/29; A61K 8/41
USPC ........................................... 424/76.1
See application file for complete search history.

(56) References Cited

U.S. PATENT DOCUMENTS

| | | | | |
|---|---|---|---|---|
| 5,690,922 | A * | 11/1997 | Mouri ........................ | D01F 8/14 424/76.1 |
| 5,872,072 | A * | 2/1999 | Mouri ................ | B01D 53/8634 502/343 |
| 8,328,917 | B2 * | 12/2012 | Garfield ................. | B01J 37/347 424/688 |
| 2003/0100445 | A1 * | 5/2003 | Ueda .................... | B01J 20/3236 502/185 |
| 2009/0285768 | A1 * | 11/2009 | Baker .................... | A61K 8/416 424/70.2 |
| 2012/0308623 | A1 * | 12/2012 | Taxt-Lamolle ......... | A61P 17/02 977/773 |
| 2013/0253073 | A1 * | 9/2013 | Ling .................. | B01D 53/8634 502/200 |

* cited by examiner

*Primary Examiner* — Eisa B Elhilo
(74) *Attorney, Agent, or Firm* — Bridgeway IP Law Group, PLLC; Sang Ho Lee; Hyun Woo Shin

(57) ABSTRACT

Provided is an antibacterial deodorant containing a titanium dioxide photocatalyst, including: a titanium dioxide photocatalyst; and a composition for antibacterial deodorization, wherein the titanium dioxide photocatalyst includes titanium dioxide ($TiO_2$), copper (Cu), and magnesium (Mg).

6 Claims, No Drawings

ANTIBACTERIAL DEODORANT CONTAINING TITANIUM DIOXIDE PHOTOCATALYST

CROSS-REFERENCE TO RELATED APPLICATIONS

This application claims priority under 35 U.S.C. § 119 to Korean Patent Application No. 10-2021-0021962, filed on Feb. 18, 2021, in the Korean Intellectual Property Office, the disclosure of which is incorporated herein by reference in its entirety.

TECHNICAL FIELD

The following disclosure relates to an antibacterial deodorant containing a titanium dioxide photocatalyst.

BACKGROUND

Coronavirus disease 19 (COVID-19) is a respiratory infectious disease caused by a new type of Coronavirus (SARS-CoV-2) that first emerged in Wuhan, China in December 2019 and has been spreading throughout China and the world. To prevent infection with the Coronavirus, only by wearing a mask correctly, washing hands frequently, and not touching eyes, nose or mouth are able to prevent most of the coronavirus infection.

A titanium dioxide photocatalyst may have strong chemical sterilization activity due to OH radicals formed by light energy irradiation.

Regarding a crystal structure, titanium dioxide ($TiO_2$) has a rutile structure and an anatase structure. Titanium dioxide having the anatase crystal structure has stronger oxidation energy than titanium dioxide having the rutile crystal structure. This characteristic makes titanium dioxide having the anatase crystal structure more advantageous for being used as a photocatalyst.

However, anatase titanium dioxide ($TiO_2$) exhibits photoresolution only under ultraviolet conditions, and the anatase titanium dioxide itself does not react in the visible light region that accounts for most of the sunlight, but exhibits the photoresolution only when irradiated with ultraviolet light employing special light sources such as an ultraviolet(UV) lamp, and the like. Thus, research on a photocatalyst capable of reacting in the visible light region that accounts for most of the sunlight, is being actively conducted.

In addition, when an antibacterial deodorant is attempted to be manufactured by adding a pure titanium dioxide photocatalyst without special processing, dispersion force may be deteriorated due to the size of the titanium dioxide photocatalyst itself.

Therefore, there is a need for the development of an antibacterial deodorant having not only improved photocatalytic efficiency in the visible light region, but also excellent dispersion force by including a titanium dioxide photocatalyst capable of being formed to have a specific particle diameter.

SUMMARY

An embodiment of the present disclosure is directed to providing an antibacterial deodorant containing a titanium dioxide photocatalyst having improved photocatalytic efficiency in the visible light region and excellent dispersion force.

All of the above and other objects of the present disclosure may be achieved by the present disclosure described below.

In one general aspect, there is provided an antibacterial deodorant containing a titanium dioxide photocatalyst.

The antibacterial deodorant containing a titanium dioxide photocatalyst includes a titanium dioxide photocatalyst and a composition for antibacterial deodorization, wherein the titanium dioxide photocatalyst includes titanium dioxide ($TiO_2$), copper (Cu), and magnesium (Mg).

The titanium dioxide photocatalyst may have a content of 1 to 5% by weight.

A weight ratio of the copper (Cu) and magnesium (Mg) may be 1:1.8 to 1:3.2.

The composition for antibacterial deodorization may include 1 to 5% by weight of surfactant; 1 to 5% by weight of caustic soda; 1 to 5% by weight of triethanolamine (TEA); 5 to 15% by weight of butyl glycol (BDG); 2 to 8% by weight of isopropyl alcohol (IPA); and remaining amount of water.

The composition for antibacterial deodorization may further include 0.01 to 0.10% by weight of polystyrene sulfate.

The composition for antibacterial deodorization may further include 1 to 5% by weight of alkyldimethylbenzene.

The composition for antibacterial deodorization may further include 0.01 to 2% by weight of citric acid.

In the titanium dioxide photocatalyst, copper (Cu) and magnesium (Mg) may be partially eutectic.

The titanium dioxide photocatalyst may include a titanium dioxide photocatalyst containing 1 to 15% by weight of the copper (Cu) and magnesium (Mg).

The titanium dioxide photocatalyst may further include 2 to 20% by weight of zirconia ($ZrO_2$).

The zirconia ($ZrO_2$) may have an average particle diameter (D50) larger than that of titanium dioxide ($TiO_2$).

The titanium dioxide photocatalyst may have an average particle diameter (D50) of 100 μm to 500 μm.

The titanium dioxide photocatalyst may include 0.01 to 3% by weight of silver (Ag) on a surface thereof.

A weight ratio of the magnesium (Mg) and silver (Ag) may be 1.3:1 to 2:1.

The silver (Ag) may have an average particle diameter (D50) of 10 nm to 25 nm.

DETAILED DESCRIPTION OF EMBODIMENTS

Hereinafter, specific embodiments of the present application will be described in more detail. However, the technology disclosed in the present application is not limited to the specific embodiments described herein and may be embodied in various forms.

The specific embodiments introduced herein are provided so that the disclosed content may be thorough and complete, and the spirit of the present application may be sufficiently conveyed to those skilled in the art. Further, although only some of the components are shown for convenience of description, those skilled in the art will be able to easily understand the remaining parts of the components.

In addition, those having ordinary skill in the relevant field will be able to implement the spirit of the present application in various other forms within the scope that does not depart from the technical spirit of the present application.

Meanwhile, the expression in the singular described in the present application should be understood to include plural expressions unless the context clearly indicates otherwise, and it will be understood that the terms "comprises", "have", and the like, specify the presence of stated features, numerals, steps, operations, components, parts, or a combination thereof, but do not preclude, in advance, the presence or addition possibility of one or more other features, numerals, steps, operations, components, parts, or a combination thereof.

In addition, in the present specification, 'X to Y' representing a range may indicate 'X or more and Y or less', and 'part by weight' may indicate a ratio between component contents.

Antibacterial Deodorant Containing Titanium Dioxide Photocatalyst

The antibacterial deodorant containing a titanium dioxide photocatalyst of the present disclosure includes a titanium dioxide photocatalyst; and a composition for antibacterial deodorization, wherein the titanium dioxide photocatalyst includes titanium dioxide ($TiO_2$), copper (Cu), and magnesium (Mg).

Titanium dioxide ($TiO_2$) is a photocatalyst in which when irradiated with near-ultraviolet light having a wavelength of about 387 nm or less, the irradiated light energy (hv) is absorbed to generate electrons (e) in a conduction band (CB) and holes (h) in a valence band (VB). The electron (e)-hole (h) pair thus generated in titanium dioxide recombines within a few seconds, but when reacting with moisture ($H_2O$) and oxygen ($O_2$) in the air before recombination, the pair is decomposed into OH radicals and $O_2^-$ radicals. In addition, the energy band gap of titanium dioxide ($TiO_2$) is about 3.2 Ev, and the radical decomposition reaction may proceed as described above even when a small amount of current exceeding the above band gap is applied.

Since the OH radical has a very excellent ability to oxidize and decompose strong organic substances, the radical decomposes odor substances, viruses, and germs such as bacteria, and the like, that are always present in the air, thereby forming water and carbon dioxide. Therefore, the titanium dioxide photocatalyst may exhibit strong chemical sterilization activity and deodorization effect due to OH radicals generated by light energy irradiation.

Thus, the antibacterial deodorant containing the titanium dioxide photocatalyst may be carried or placed inside the house for use, and may also be used by spraying on textile products such as masks and clothing, bedding products such as blankets and pillows, and the like.

The antibacterial deodorant may have a content of 1 to 5% by weight, and specifically 1.5 to 3% by weight, of the titanium dioxide photocatalyst. Within this range, the antibacterial deodorant may have excellent chemical sterilization activity and deodorization effect, and provide economic advantages.

The titanium dioxide may have an average particle diameter (D50) of 1 nm to 100 nm, specifically 5 nm to 80 nm.

The titanium dioxide may include two or more types of titanium dioxide having different average particle diameters (D50). In this case, a photocatalyst efficiency according to compactness of the photocatalyst is improved.

For example, the titanium dioxide ($TiO_2$) may include first and second titanium dioxide ($TiO_2$) having different average particle diameters (D50), wherein the first titanium dioxide ($TiO_2$) may have an average particle diameter (D50) of 1 nm to 70 nm, and specifically 10 nm to 50 nm, and the second titanium dioxide ($TiO_2$) may have an average particle diameter (D50) of 20 nm to 100 nm, and specifically 20 nm to 80 nm. Further, a ratio of the average particle diameter (D50) between the first titanium dioxide ($TiO_2$) and the second titanium dioxide ($TiO_2$) may be 1:0.4 to 1:0.6. In the above range of the average particle diameter, the titanium dioxide photocatalyst may become more dense and maximize the photocatalytic efficiency.

In the titanium dioxide photocatalyst, a weight ratio of copper (Cu) and magnesium (Mg) may be 1:1.8 to 1:3.2.

The copper (Cu) and magnesium (Mg) may be included in the catalyst component to increase a light absorption rate in the visible light region, thereby not only improving the photocatalytic efficiency, but also improving binding ability of titanium dioxide ($TiO_2$) and other components. Further, a catalytic activity may be exhibited even at a lower current, or the catalytic activity may be higher even at the same current, and thus the photocatalytic efficiency is excellent.

In particular, in the titanium dioxide photocatalyst of the present disclosure, by applying the weight ratio of copper (Cu) and magnesium (Mg) to the range of 1:1.8 to 1:3.2, and specifically 1:2 to 1:2.8 so as to be close to the eutectic point, it is possible to significantly lower the temperature of a manufacturing process of the titanium dioxide photocatalyst, which may minimize transition to the rutile crystal structure, thereby maximizing the photocatalyst efficiency.

In the titanium dioxide photocatalyst, the copper (Cu) and magnesium (Mg) may be partially eutectic. In this case, the copper (Cu) and magnesium (Mg) components may improve the binding ability between the titanium dioxide photocatalyst components.

The titanium dioxide photocatalyst may include 1 to 15% by weight, specifically 1 to 12% by weight, and more specifically 1 to 10% by weight of the copper (Cu) and magnesium (Mg).

By adjusting the percent by weight (wt %) of copper (Cu) and magnesium (Mg) included in the titanium dioxide photocatalyst, the titanium dioxide photocatalyst may be manufactured to have a particle diameter suitable for the antibacterial deodorant.

The titanium dioxide photocatalyst may have an average particle diameter (D50) of 100 μm to 500 μm, specifically 150 μm to 400 μm, and more specifically 200 μm to 300 μm. Within this range, there is an advantage in that dispersion force is excellent when spraying the antibacterial deodorant.

In the above-described ranges of copper (Cu) and magnesium (Mg), the titanium dioxide photocatalyst may be manufactured to have a particle diameter suitable for spraying the antibacterial deodorant.

In another embodiment, the titanium dioxide photocatalyst may further include 2 to 20% by weight of zirconia ($ZrO_2$)

The zirconia ($ZrO_2$) may be included in the titanium dioxide photocatalyst to improve stability and durability. Specifically, the zirconia ($ZrO_2$) is a heat-resistant material having a high melting temperature (about 2,700° C.), and has excellent material properties such as low thermal conductivity, wide chemical stability from acidic to alkaline region, low thermal expansion, high hardness, and the like.

Since the zirconia ($ZrO_2$) as a photocatalyst may also be used together with titanium dioxide to maximize the photocatalyst efficiency and improve the durability of the titanium dioxide photocatalyst, it is possible to minimize the phenomenon that the titanium dioxide photocatalyst is broken or delaminated.

The zirconia ($ZrO_2$) may be included in a content of 2 to 20% by weight, specifically 5 to 15% by weight of the titanium dioxide photocatalyst. Within this range, the improvement effect of the photocatalytic efficiency and the durability of the titanium dioxide photocatalyst is excellent.

The zirconia ($ZrO_2$) may have an average particle diameter (D50) larger than that of titanium dioxide ($TiO_2$).

In this case, the titanium dioxide photocatalyst has excellent durability improvement effect. Specifically, the zirconia ($ZrO_2$) may have an average particle diameter (D50) of more than 100 nm and 800 nm or less, for example, 200 nm to 500 nm.

The titanium dioxide photocatalyst may include 0.01 to 3% by weight of silver (Ag) on a surface thereof.

The silver (Ag) is adsorbed to oxygen atoms when oxygen molecules come into contact with the surface, and these oxygen atoms may oxidize and dissolve cell membranes of bacteria and viruses, and the like, to kill the bacteria and viruses, thereby exhibiting sterilization and antibacterial effects.

The silver (Ag) may be included in a content of 0.01 to 5% by weight, specifically 0.1 to 4% by weight, and more specifically 0.5 to 3% by weight of the titanium dioxide photocatalyst. Within this range, it is possible to further enhance the antibacterial and deodorization effect of the antibacterial deodorant by improving the photocatalytic efficiency on the surface of the titanium dioxide photocatalyst. In addition, since the silver (Ag) is included only on the surface of the titanium dioxide photocatalyst, it is economical in that the manufacturing cost is low.

A weight ratio of the magnesium (Mg) and silver (Ag) may be 1.3:1 to 2:1.

By applying the weight ratio of magnesium (Mg) and silver (Ag) in the titanium dioxide photocatalyst to the range of 1.3:1 to 2:1, specifically 1:5 to 1.8:1 so as to be close to the eutectic point, the silver (Ag) component may be effectively bound on the surface of the titanium dioxide photocatalyst to further improve the sterilization, antibacterial and deodorization effects of the titanium dioxide photocatalyst.

The silver (Ag) may have an average particle diameter (D50) of 10 nm to 25 nm.

A sterilization action of the silver (Ag) is achieved through a surface reaction. Forming the silver in a nano size indicates that a surface area of the silver with the same mass is greatly increased, and thus the sterilization and antibacterial ability of the silver is also maximized. In other words, since the surface area and the particle size are in inverse proportion to each other, as the surface area becomes larger, the antibacterial ability of silver is further improved.

The silver (Ag) may have the average particle diameter (D50) of 10 nm to 25 mm, specifically 12 nm to 22 mm, and more specifically 14 nm to 20 mm. Within this range, the silver has strong sterilization and antibacterial properties, and it is harmless to human body even if the silver (Ag) is removed from the surface of the titanium dioxide photocatalyst and ingested by humans.

The composition for antibacterial deodorization may include 1 to 5% by weight of surfactant; 1 to 5% by weight of caustic soda; 1 to 5% by weight of triethanolamine (TEA); 5 to 15% by weight of butyl glycol (BDG); 2 to 8% by weight of isopropyl alcohol (IPA); and remaining amount of water.

The surfactant has a hydrophilic group and a hydrophobic group, which serves to disperse and dissociate contaminants from materials to be washed by actions of the surfactant such as permeation, dispersion, emulsification, foaming, adsorption, prevention of recontamination, and the like.

The surfactant may have a content of 1 to 5% by weight, and specifically 2 to 4% by weight. Within this range, it is possible to effectively dissociate the contaminants by lowering surface tension between the contaminants adhering to the materials to be washed and the composition for antibacterial deodorization.

The caustic soda serves to adjust the pH of the composition for antibacterial deodorization and to improve the antibacterial ability of the composition for antibacterial deodorization.

The caustic soda may have a content of 1 to 5% by weight, and specifically 2 to 4% by weight. Within this range, it is possible to create a pH environment suitable for the antibacterial deodorant, and to increase the antibacterial and deodorization abilities of the composition for antibacterial deodorization.

The triethanolamine (TEA) serves to adjust the pH of the composition for antibacterial deodorization.

The triethanolamine (TEA) may have a content of 1 to 5% by weight, and specifically 1.5 to 3% by weight. Within this range, it is possible to create a pH environment suitable for the antibacterial deodorant.

The butyl glycol (BDG) prevents crystallization of substances that are not soluble in the composition for antibacterial deodorization, and helps dissolve substances that are not soluble in water. In addition, the butyl glycol itself has an antimicrobial effect, which serves to prevent spoilage of the composition for antibacterial deodorization.

The butyl glycol (BDG) may have a content of 5 to 15% by weight, and specifically 7 to 12% by weight. Within this range, it is possible to increase the solubility of the composition for antibacterial deodorization and to have excellent antimicrobial effect.

The composition for antibacterial deodorization may further include 0.01 to 0.05% by weight of polystyrene sulfate.

The polystyrene sulfate may have an antibacterial action that kills the activity of the bacteria by immobilizing the bacteria.

The polystyrene sulfate may have a content of 0.01 to 0.10% by weight, and specifically 0.03 to 0.06% by weight. Within this range, it is possible to exhibit an antibacterial effect.

The composition for antibacterial deodorization may further include 1 to 5% by weight of alkyldimethylbenzene.

The alkyldimethylbenzene exerts a sterilization effect by extensively acting on various pathogenic microorganisms such as viruses, bacteria or fungi, on the basis of strong oxidizing power, while simultaneously being released due to aromatic properties of the benzene ring.

The alkyldimethylbenzene may have a content of 1 to 5% by weight, and specifically 2 to 4% by weight. Within this range, it is possible to exhibit sterilization and deodorization effects.

For example, the alkyldimethylbenzene may be hexyldimethylbenzene, but is not limited thereto.

The composition for antibacterial deodorization may further include a fragrance agent to add a specific fragrance. The fragrance agent may include one or more selected from the group consisting of gentiana extract, sage extract, chamomile extract, lavender extract, sophora root extract, propolis extract, peppermint oil, mastic oil, myrrh tincture, ratania tincture, cypress oil, and eucalyptus oil. The fragrance agent may have a content of 0.1 to 3% by weight, and specifically, 0.1 to 1% by weight, and when the fragrance agent and the alkyldimethylbenzene are included in a weight ratio of 1:1 to 1:3, it is possible to exhibit a more excellent fragrance effect.

The composition for antibacterial deodorization may further include 0.01 to 2% by weight of citric acid.

The citric acid may have the antibacterial efficacy by adjusting the acidity to inhibit bacterial growth, and may increase the storage period of the composition for antibacterial deodorization by inhibiting coagulation of the composition.

The citric acid may have a content of 0.01 to 2% by weight, and specifically 0.03 to 1.5% by weight. Within this range, the antibacterial effect, improvement of preservation period, and an anti-coagulation effect of the composition for antibacterial deodorization are enhanced.

Method for Manufacturing Antibacterial Deodorant Containing Titanium Dioxide Photocatalyst A method for manufacturing an antibacterial deodorant containing titanium dioxide photocatalyst may include forming a mixture of titanium dioxide ($TiO_2$) powder, copper (Cu), and magnesium (Mg); primary heat-treating the mixture; adding silver (Ag) to the heat-treated titanium dioxide photocatalyst, followed by secondary heat-treatment; and mixing the secondary heat-treated titanium dioxide photocatalyst with a composition for antibacterial deodorization.

The titanium dioxide ($TiO_2$) powder, copper (Cu), and magnesium (Mg) may be substantially the same as those described in the titanium dioxide photocatalyst according to an aspect of the present disclosure.

The primary heat-treatment may be performed at 485° C. to 490° C. under $H_2$/Ar atmosphere.

In another embodiment, the primary heat-treatment may be performed at a temperature exceeding 490° C. under the $H_2$/Ar atmosphere.

By applying a weight ratio of copper (Cu) and magnesium (Mg) contained in the titanium dioxide photocatalyst of the present disclosure to a range of 1:1.8 to 1:3.2, and specifically 1:2 to 1:2.8, the copper (Cu) and magnesium (Mg) may be partially eutectic in the above-described heat treatment temperature range, thereby sufficiently adding a binding ability between the components constituting the photocatalyst.

In particular, the content of the copper (Cu) and magnesium (Mg) components may affect the particle diameter of the titanium dioxide photocatalyst, and specifically, the copper (Cu) and magnesium (Mg) may be included in a content of 1 to 15% by weight of the titanium dioxide photocatalyst, thereby controlling the average particle diameter (D50) of the titanium dioxide photocatalyst to be 100 μm to 500 μm. When the antibacterial deodorant is sprayed in the average particle diameter range, spraying power may be excellent and light absorption in the visible light region may be increased to exhibit an effect of improving photocatalyst efficiency, thereby making it possible to form a titanium dioxide photocatalyst capable of effectively providing the antibacterial action.

The secondary heat-treatment may be performed at 450° C. to 485° C., and specifically 472° C. to 485° C. under the $H_2$/Ar atmosphere after performing the primary first heat-treatment and adding silver (Ag) to the titanium dioxide photocatalyst containing titanium dioxide ($TiO_2$), copper (Cu), and magnesium (Mg). By applying a weight ratio of magnesium (Mg) and silver (Ag) contained in the titanium dioxide photocatalyst of the present disclosure to be 1.3:1 to 2:1, magnesium (Mg) and silver (Ag) may be partially eutectic in the heat treatment temperature range, and thus silver (Ag) may be bound to the surface of the titanium dioxide photocatalyst.

The silver (Ag) is adsorbed to oxygen atoms when oxygen molecules come into contact with the surface, and these oxygen atoms may oxidize and dissolve cell membranes of bacteria and viruses, and the like, to kill the bacteria and viruses, thereby exhibiting sterilization and antibacterial effects. The silver (Ag) component is effectively bound on the surface of the titanium dioxide photocatalyst to obtain a titanium dioxide photocatalyst with improved sterilization and antibacterial effects.

In another embodiment, in the forming of the mixture, the mixture may be formed to further include zirconia ($ZrO_2$), wherein the zirconia ($ZrO_2$) may be substantially the same as described in the titanium dioxide photocatalyst according to an aspect of the present disclosure.

In the mixing of the secondary heat-treated titanium dioxide photocatalyst and the composition for antibacterial deodorization, the composition for antibacterial deodorization may be substantially the same as described in the composition for antibacterial deodorization according to an aspect of the present disclosure.

The composition for antibacterial deodorization may be formed by sequentially mixing 1 to 5% by weight of surfactant, 1 to 5% by weight of caustic soda, 1 to 5% by weight of triethanolamine (TEA), 5 to 15% by weight of butyl glycol (BDG), 2 to 8% by weight of isopropyl alcohol (IPA), and remaining amount of water in a stirrer, followed by stirring for 60 to 75 minutes and taking the mixture out of the stirrer.

The second heat-treated titanium dioxide photocatalyst and the taken composition for antibacterial deodorization may be mixed to manufacture the antibacterial deodorant containing the titanium dioxide photocatalyst.

In another embodiment, the composition for antibacterial deodorization may be formed to further include 0.01 to 0.05% by weight of polystyrene sulfate.

In still another embodiment, the composition for antibacterial deodorization may be formed to further include 1 to 5% by weight of alkyldimethylbenzene.

In still another embodiment, the composition for antibacterial deodorization may be formed to further include 0.01 to 2% by weight of citric acid.

EXAMPLES

Example 1

95% by weight of titanium dioxide ($TiO_2$, Aldrich), 1.4% by weight of copper (Cu), and 3.6% by weight of magnesium (Mg) were mixed, and the obtained mixture was put into a tube furnace and heated at 530° C. for 5 hours under $H_2$/Ar atmosphere. Then, the mixture was stirred in 1.0M HCl solution for 24 hours, washed with water to remove acid, and dried to manufacture a titanium dioxide photocatalyst.

3% by weight of caustic soda was dissolved and stirred in 76.5% by weight of water having a pH of 7.5 or less. After 5 minutes, 3% by weight of a surfactant was added to the water in which the caustic soda was dissolved, followed by stirring for 5 minutes using a stirrer. To the surfactant-added mixture, 2.5% by weight of triethanolamine (TEA) was added and stirred for 5 minutes. While 10% by weight of butyl glycol (BDG) was added to the mixture in which triethanolamine was added, the mixture was stirred for 50 minutes. While 5% by weight of isopropyl alcohol (IPA) was added to the mixture in which butyl glycol was added, the mixture was stirred continuously for 10 to 15 minutes, and then taken out of the stirrer to prepare a composition for antibacterial deodorization.

An antibacterial deodorant containing the titanium dioxide photocatalyst was formed by mixing 2.5% by weight of the titanium dioxide photocatalyst and 97.5% by weight of the composition for antibacterial deodorization as prepared above.

The titanium dioxide photocatalyst had an average particle diameter (D50) of 250 μm.

Example 2

An antibacterial deodorant containing a titanium dioxide photocatalyst was formed in the same manner as in Example 1, except that 0.05% by weight of polystyrene sulfate and 76.45% by weight of water were contained in the composition for antibacterial deodorization.

Example 3

An antibacterial deodorant containing a titanium dioxide photocatalyst was formed in the same manner as in Example 1, except that 3% by weight of alkyldimethylbenzene and 73.5% by weight of water were contained in the composition for antibacterial deodorization.

Example 4

92.9% by weight of titanium dioxide ($TiO_2$, Aldrich), 1.4% by weight of copper (Cu), and 3.6% by weight of magnesium (Mg) were mixed, and the obtained mixture was put into a tube furnace, and heated at 530° C. for 5 hours under $H_2$/Ar atmosphere. Then, the mixture was stirred in 1.0M HCl solution for 24 hours, washed with water to remove acid, and dried to manufacture a titanium dioxide photocatalyst. 97.9% by weight of the titanium dioxide photocatalyst and 2.1% by weight of silver (Ag) were mixed, and the mixture was put into a tube furnace, heated at 495° C. for 5 hours under $H_2$/Ar atmosphere, and then cooled at 472° C. after heating.

3% by weight of caustic soda was dissolved and stirred in 76.5% by weight of water having a pH of 7.5 or less. After 5 minutes, 3% by weight of a surfactant was added to the water in which the caustic soda was dissolved and stirred for 5 minutes using a stirrer. 2.5% by weight of triethanolamine (TEA) was added to the surfactant-added mixture and stirred for 5 minutes. While 10% by weight of butyl glycol (BDG) was added to the mixture in which triethanolamine was added, the mixture was stirred for 50 minutes. While 5% by weight of isopropyl alcohol (IPA) was added to the mixture in which butyl glycol was added, the mixture was stirred continuously for 10 to 15 minutes, and then taken out of the stirrer to prepare a composition for antibacterial deodorization.

An antibacterial deodorant containing a titanium dioxide photocatalyst was formed by mixing 2.5% by weight of a titanium dioxide photocatalyst containing silver (Ag) on a surface of the titanium dioxide photocatalyst and 97.5% by weight of the composition for antibacterial deodorization.

The titanium dioxide photocatalyst had an average particle diameter (D50) of 270 μm, and silver (Ag) had an average particle diameter (D50) of 17 nm.

Example 5

An antibacterial deodorant containing a titanium dioxide photocatalyst was formed in the same manner as in Example 1, except that 0.05% by weight of polystyrene sulfate and 76.45% by weight of water were contained in the composition for antibacterial deodorization.

Example 6

An antibacterial deodorant containing a titanium dioxide photocatalyst was formed in the same manner as in Example 1, except that 3% by weight of alkyldimethylbenzene and 73.5% by weight of water were contained in the composition for antibacterial deodorization.

Example 7

An antibacterial deodorant containing a titanium dioxide photocatalyst was formed in the same manner as in Example 4, except that 0.05% by weight of polystyrene sulfate, 3% by weight of alkyldimethylbenzene, and 73.45% by weight of water were contained in the composition for antibacterial deodorization.

Example 8

An antibacterial deodorant containing a titanium dioxide photocatalyst was formed in the same manner as in Example 4, except that 0.05% by weight of polystyrene sulfate, 3% by weight of alkyldimethylbenzene, 0.5% by weight of citric acid; and 72.95% by weight of water were contained in the composition for antibacterial deodorization.

Comparative Example 1

3% by weight of caustic soda was dissolved and stirred in 76.5% by weight of water having a pH of 7.5 or less. After 5 minutes, 3% by weight of a surfactant was added to the water in which the caustic soda was dissolved, followed by stirring for 5 minutes using a stirrer. 2.5% by weight of triethanolamine (TEA) was added to the surfactant-added mixture and stirred for 5 minutes. While 10% by weight of butyl glycol (BDG) was added to the mixture in which triethanolamine was added, the mixture was stirred for 50 minutes. While 5% by weight of isopropyl alcohol (IPA) was added to the mixture in which butyl glycol was added, the mixture was stirred continuously for 10 to 15 minutes, and then taken out of the stirrer to prepare a composition for antibacterial deodorization.

Method for Measuring Antibacterial Activity

The prepared specimens of Examples and Comparative Examples were plated on paper discs. Then, antibacterial abilities of the specimens were measured by arranging the discs at regular intervals under aseptic manipulation on media on which strains were smeared, and culturing the strains for 2 days. The antibacterial ability of the specimen was evaluated by measuring a diameter (mm) of a growth inhibition region of the strain generated around the paper disc.

As test strains, E. coli, Staphylococcus aureus, Salmonella, Pseudomonas aeruginosa, and black mold were used, and respective strains were purchased from the American Type Culture Collection (ATCC, U.S.A.) and used. The strains were inoculated into a medium (malt extract agar 6%, ox-bile 2%, Tween-40 1%, and glycerol mono-oleate 0.25%) and then cultured at 37° C. for 24 hours.

The cultured strains were diluted at a ratio of 1/100 and streak-plated on a solid medium of a plate. The paper discs were arranged, and after 2 days, a growth inhibition ring (mm) was measured. The size of the inhibition ring formed around the paper disc means an antibacterial ability, and the larger the inhibition ring, the more excellent the antibacterial ability. The measurement results of the growth inhibition rings are shown in Table 1 below.

TABLE 1

| Classification | Escherichia coli | Staphylococcus aureus | Pseudomonas aeruginosa | Salmonella | Black mold |
|---|---|---|---|---|---|
| Example 1 | 19.9 | 12.0 | 12.5 | 14.5 | 10.0 |
| Example 2 | 19.7 | 21.6 | 15.2 | 15.2 | 10.3 |
| Example 3 | 19.5 | 14.7 | 23.9 | 14.4 | 10.2 |
| Example 4 | 19.6 | 13.5 | 14.4 | 22.5 | 9.9 |
| Example 5 | 19.5 | 22.1 | 13.4 | 23.3 | 10.2 |
| Example 6 | 19.8 | 15.3 | 24.3 | 22.8 | 10.1 |
| Example 7 | 19.6 | 23.0 | 24.5 | 23.7 | 10.1 |
| Example 8 | 20.1 | 23.7 | 24.9 | 24.2 | 13.2 |
| Comparative Example 1 | 14.5 | 11.9 | 11.4 | 12.3 | 9.9 |

As shown in Table 1, when the antibacterial deodorant containing the titanium dioxide photocatalyst was treated, the antibacterial activity against E. coli was significantly increased.

In particular, as compared with Comparative Example 1, the antibacterial deodorants containing polystyrene sulfate according to Examples 2 and 5 showed increased antibacterial activity against Staphylococcus aureus, the antibacterial deodorants containing alkyldimethylbenzene according to Examples 3 and 7 showed increased antibacterial activity against Pseudomonas aeruginosa, and the antibacterial deodorants containing silver according to Examples 4 to 8 showed increased antibacterial activity against Salmonella, and thus it may be appreciated that the sterilization power of the antibacterial deodorant containing the titanium dioxide photocatalyst of the present disclosure may be further increased.

The present disclosure provides an antibacterial deodorant containing a titanium dioxide photocatalyst having improved photocatalytic efficiency in the visible light region and excellent dispersion force.

Although the Examples of the present disclosure have been described above, the present disclosure is not limited to the above Examples, but may be made in a variety of different forms. Those having ordinary skill in the art to which the present disclosure pertains will appreciate that the present disclosure may be implemented in other specific forms without changing the technical spirit or essential features of the present disclosure. Therefore, it should be understood that the embodiments described above are illustrative but not restrictive in all respects.

What is claimed is:

1. An antibacterial deodorant comprising:
    a titanium dioxide photocatalyst; and
    a composition for antibacterial deodorization,
    wherein the titanium dioxide photocatalyst includes titanium dioxide ($TiO_2$); copper (Cu); and magnesium (Mg).

2. The antibacterial deodorant according to claim 1, wherein the titanium dioxide photocatalyst has a content of 1 to 5% by weight, and
    a weight ratio of the copper (Cu) and magnesium (Mg) is 1:1.8 to 1:3.2.

3. The antibacterial deodorant according to claim 1, wherein the composition for antibacterial deodorization includes:
    1 to 5% by weight of surfactant;
    1 to 5% by weight of caustic soda;
    1 to 5% by weight of triethanolamine (TEA);
    5 to 15% by weight of butyl glycol (BDG);
    2 to 8% by weight of isopropyl alcohol (IPA); and
    remaining amount of water.

4. The antibacterial deodorant according to claim 3, wherein the composition for antibacterial deodorization further includes:
    1 to 5% by weight of alkyldimethylbenzene; and
    0.1 to 3% by weight of a fragrance agent,
    wherein the fragrance agent includes one or more selected from the group consisting of gentiana extract, sage extract, chamomile extract, lavender extract, sophora root extract, propolis extract, peppermint oil, mastic oil, myrrh tincture, ratania tincture, cypress oil, and eucalyptus oil.

5. The antibacterial deodorant according to claim 1, wherein the titanium dioxide photocatalyst further includes 2 to 20% by weight of zirconia ($ZrO_2$).

6. The antibacterial deodorant according to claim 1, wherein the titanium dioxide photocatalyst further includes 0.1 to 5% by weight of silver (Ag) on a surface of the titanium dioxide photocatalyst.

* * * * *